(12) United States Patent
Singh et al.

(10) Patent No.: US 11,964,263 B2
(45) Date of Patent: Apr. 23, 2024

(54) CATALYST FOR THE PRODUCTION OF CARBOXYLIC ACID ESTER

(71) Applicant: SBI FINE CHEMICALS INC., Edmonton (CA)

(72) Inventors: Inder Pal Singh, Edmonton (CA); Shradha Singh, Edmonton (CA); Bharat Mistry, Edmonton (CA); Zhiyong Li, Edmonton (CA)

(73) Assignee: SBI FINE CHEMICALS INC., Edmonton (CA)

( * ) Notice: Subject to any disclaimer, the term of this patent is extended or adjusted under 35 U.S.C. 154(b) by 573 days.

(21) Appl. No.: 17/263,624

(22) PCT Filed: Aug. 16, 2019

(86) PCT No.: PCT/CA2019/051115
§ 371 (c)(1),
(2) Date: Jan. 27, 2021

(87) PCT Pub. No.: WO2020/034038
PCT Pub. Date: Feb. 20, 2020

(65) Prior Publication Data
US 2021/0162386 A1 Jun. 3, 2021

Related U.S. Application Data

(60) Provisional application No. 62/765,036, filed on Aug. 17, 2018.

(51) Int. Cl.
| | | |
|---|---|---|
| *B01J 29/80* | (2006.01) |
| *B01J 23/06* | (2006.01) |
| *B01J 29/06* | (2006.01) |
| *B01J 29/08* | (2006.01) |
| *B01J 29/18* | (2006.01) |
| *B01J 29/70* | (2006.01) |
| *B01J 35/00* | (2024.01) |
| *B01J 35/10* | (2006.01) |
| *B01J 35/30* | (2024.01) |
| *B01J 35/61* | (2024.01) |
| *B01J 35/63* | (2024.01) |
| *B01J 35/64* | (2024.01) |
| *C07C 67/02* | (2006.01) |
| *C07C 67/03* | (2006.01) |
| *C11C 3/00* | (2006.01) |
| *C11C 3/04* | (2006.01) |

(52) U.S. Cl.
CPC ............. *B01J 29/80* (2013.01); *B01J 23/06* (2013.01); *B01J 29/061* (2013.01); *B01J 29/085* (2013.01); *B01J 29/185* (2013.01); *B01J 29/7049* (2013.01); *B01J 29/7053* (2013.01); *B01J 35/00* (2013.01); *B01J 35/19* (2024.01); *B01J 35/30* (2024.01); *B01J 35/612* (2024.01); *B01J 35/613* (2024.01); *B01J 35/633* (2024.01); *B01J 35/635* (2024.01); *B01J 35/643* (2024.01); *B01J 35/647* (2024.01); *C07C 67/02* (2013.01); *C07C 67/03* (2013.01); *C11C 3/003* (2013.01); *C11C 3/04* (2013.01); *B01J 2029/062* (2013.01); *B01J 2229/186* (2013.01)

(58) Field of Classification Search
CPC ... C11C 3/003; C11C 3/04; B01J 29/80; B01J 29/061; B01J 29/085; B01J 29/185; B01J 29/7049; B01J 29/7053; B01J 23/06; B01J 35/0006; B01J 35/02; B01J 35/1009; B01J 35/1014; B01J 35/1038; B01J 35/1042; B01J 35/1057; B01J 35/1061; C07C 67/03; C07C 67/02
See application file for complete search history.

(56) References Cited

U.S. PATENT DOCUMENTS

| | | | | |
|---|---|---|---|---|
| 9,278,340 | B2 * | 3/2016 | Singh | ...................... C07C 67/03 |
| 2018/0029021 | A1 * | 2/2018 | Boal | .................... C07D 301/12 |

FOREIGN PATENT DOCUMENTS

| | | | |
|---|---|---|---|
| WO | 2014210560 | 12/2014 | |
| WO | 2017019445 | 2/2017 | |
| WO | WO-2017019445 A1 * | 2/2017 | ........... C07D 307/68 |

OTHER PUBLICATIONS

Kanghee Cho et al: "Generation of Mesoporosity in LTA Zeolites by Organosilane Surfactant for Rapid Molecular Transport in Catalytic Application", Chemistry of Materials, vol. 21, No. 23, Dec. 8, 2009, pp. 5664-5673.
Al-Ani Aqeel et al: "Catalytic performance of microporous materials for the production of renewable fuels", Journal of Porous Materials, Springer US, New York, vol. 26, No. 1, Apr. 26, 2018, pp. 69-76.
Osatiashtiani Amin et al: "On the influence of Si:Al ratio and hierarchical porosity of FAU zeolites in solid acid catalysed esterification pretreatment of bio-oil", Biomass Conversion and Biorefinery, Springer Berlin Heidelberg, Berlin/Heidelberg, vol. 7, No. 3, Apr. 5, 2017, pp. 331-342.
Abebe K Endalew et al: "Inorganic heterogeneous catalysts for biodiesel production from vegetable oils", Biomass and Bioenergy, Pergamon, Amsterdam, NL, vol. 35, No. 9, Jun. 2, 2011, pp. 3787-3809.

* cited by examiner

*Primary Examiner* — Yong L Chu
(74) *Attorney, Agent, or Firm* — NORTON ROSE FULBRIGHT CANADA LLP

(57) ABSTRACT

Catalysts and methods for use in conversion of glycerides and free fatty acids to biodiesel are described. A batch or continuous process may be used with the catalysts for transesterification of triglycerides with an alkyl alcohol to produce corresponding mono carboxylic acid esters and glycerol in high yields and purity. Similarly, alkyl and aryl carboxylic acids and free fatty acids are also converted to corresponding alkyl esters. Catalysts are capable of simultaneous esterification and transesterification under same process conditions. The described catalysts are thermostable, long lasting, and highly active.

19 Claims, 1 Drawing Sheet

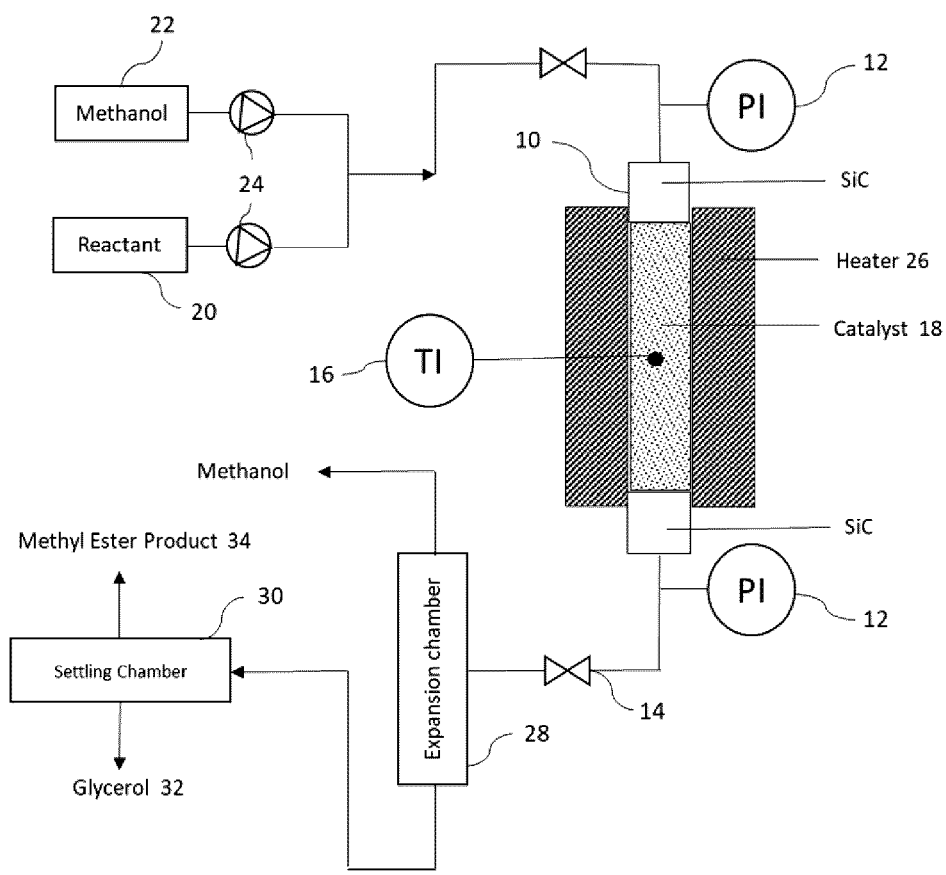

CATALYST FOR THE PRODUCTION OF CARBOXYLIC ACID ESTER

CROSS-REFERENCE TO RELATED APPLICATIONS

The present application is a U.S. National Phase of International Application No. PCT/CA2019/051115, filed on Aug. 16, 2019, and claims benefit of U.S. Provisional Application No. 62/765,036 filed Aug. 17, 2018, the content of which is hereby incorporated by reference in its entirety.

FIELD OF THE INVENTION

The present disclosure relates to the production of biodiesel from glycerides and free fatty acids.

BACKGROUND

Biodiesel is a non-toxic fuel that may be used alone or blended with petroleum diesel at any ratio to create a biodiesel blend. Biodiesel has a high-Cetane number, is essentially free of sulfur and aromatics, and is therefore a clean burning fuel, free of NOx and SOx.

Biodiesel is commonly produced by transesterification, the reaction of an alcohol with glycerides present in animal fat or vegetable oil. Generally, such reactions are catalyzed by homogeneous catalysts such as mineral acids, metal hydroxide, metal alkoxides, and carbonates. As mineral acid catalyzed reactions are slow and therefore economically non-viable, metal hydroxides such as sodium or potassium hydroxides are more commonly used as they are relatively inexpensive and suitably effective. One disadvantage to using alkaline hydroxides or carbonates in transesterification reactions is the generation of soap that compromises product yields and product quality. Glycerol (glycerin) is also produced as a byproduct, however the presence of water and soaps creates an emulsion that complicates the purification of biodiesel and the separation of glycerol from the fatty acid esters. Generally, copious amounts of acids and water are used to neutralize catalyst and remove soaps from the desirable reaction products. As a result, the increased number of steps required to obtain purified biodiesel and useable quality glycerol add tremendously to the cost of production, and also lead to a certain degree of environmental pollution.

The following equations illustrate the reactions that take place during transesterification to biodiesel by existing methods, using homogeneous catalysts.

Equation 1

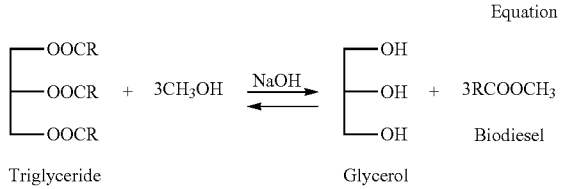

Equation 2

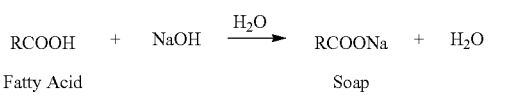

Equation 3

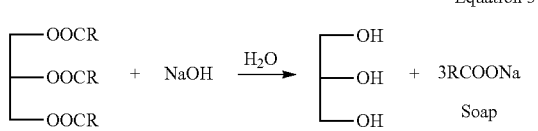

Equation 4

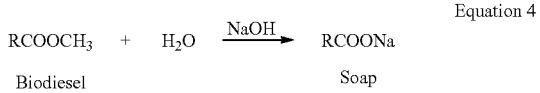

Further attempts have been made to substitute homogeneous catalysts for solid catalysts. Such replacement of homogeneous catalysts, for example with solid metal oxides and double metal cyanides (DMC), is perceived to have the advantages of simple retrieval of catalyst, elimination of soap formation and reduction of environmental pollutants. Further, the use of solid catalysts in place of homogeneous catalysts may lead to higher-quality esters and glycerol, which are more easily separable and without added cost to refine the resulting ester (U.S. Pat. No. 6,147,196). In accordance with this expectation, a number of solid catalysts have now been reported. These are generally based on metal oxides and double metal cyanides (DMC) to affect the desired transesterification reaction shown in equation 5 below.

Equation 5

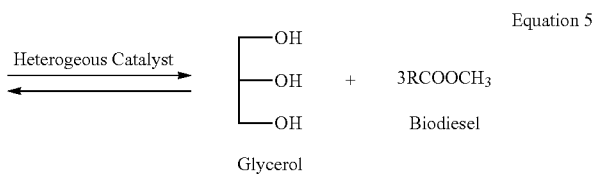

European Patent No. EP0198243 describes a solid, heterogeneous catalyst that is based on a mixture of iron oxide with alumina. This catalyst requires a very large catalyst to oil ratio, and extended contact time of more than 6 hours. Reaction temperatures of 280° C. to 320° C. are typically required, which results in coloration of the biodiesel and presence of impurities.

U.S. Pat. No. 5,908,946 describes catalysts prepared from mixtures of zinc oxide, alumina and zinc aluminate. While the catalyst does provide complete conversion to methyl ester, long reaction times and high temperatures are required. Moreover, the reaction is sensitive to the presence of water and free fatty acids. When feed oils contain free fatty acids, an esterification step must be carried out separately, prior to the transesterification reaction under a separate set of reaction conditions.

U.S. Pat. No. 7,151,187 describes catalysts made by combining two or more of titanium isopropoxide, zinc oxide, alumina, and bismuth salts using nitric acid. Use of nitric acid is not desirable, as it is corrosive, toxic, and has a negative impact on the environment. Further, the use of nitric acid also impacts the basicity of the catalyst, which may affect the transesterification reaction. Furthermore, the active form of the catalyst are their corresponding fatty acids salts or soaps, which tend to lose the efficiency rapidly (Fabiano Rosa da Silva, 2018, Energy & Fuels, 27: 2218-2225).

It has further been shown that exchange of sodium ions in the 4 Å molecular sieves (formula: $Na_{12}[(AlO_2)_{12}(SiO_2)_{12}] \cdot xH_2O$), with either $K^+$ or $Cs^+$ leads to a material with higher basicity which assists in heterogeneous transesterification catalysis. However, testing has shown that despite enhancement of the basic sites, these ion-exchanged zeolites failed to achieve complete transformation of triglycerides to biodiesel and have relatively short active life span.

A double metal cyanide (DMC) catalyst $Fe_2Zn_3(CN)_{10}$ has also been shown to transesterify oils at relatively lower temperatures. However, the slow pace of reaction leads to extended reaction time and requires excessive catalyst and reactor volume.

U.S. Pat. No. 9,278,340 describes heterogeneous catalysts comprising modified type 3 Å, 4 Å, or 5 Å zeolites for transformation of triglycerides and free fatty acids in to biodiesel, under milder temperature and pressure conditions. However, the micropore size of the zeolites used hinders the large triglyceride molecule's access to the active sites located inside the cavities of the catalyst, therefore limiting the effectiveness of the catalyst which in turn results in longer reaction time or residence time. From an economic point of view, further improvement of catalyst performance to increase the efficiency of catalyst is necessary.

There is accordingly still a need to provide solid, heterogeneous catalysts that do not exhibit the shortcomings discussed above.

SUMMARY

In accordance with one aspect of the disclosure, there is provided a solid, heterogeneous catalyst composition for use in an esterification and/or transesterification reaction. The catalyst comprises at least one Mesoporous Linde Type A (MLTA) zeolite, alone or in combination with at least one ion exchanged type 3 Å, 4 Å, 5 Å zeolite (Modified Molecular Sieves, MMS), and/or at least one metal oxide.

In accordance with another aspect of the disclosure there is provided a method for performing an esterification and/or a transesterification of a starting material, comprising reacting the starting material with an alcohol in the presence of a catalyst, wherein the catalyst comprises at least one MLTA zeolite; and/or at least one ion exchanged MMS selected from the group consisting of MMS-3 ÅK, MMS-3 ÅCs, MMS-4 ÅK, MMS-4 ÅCs, MMS-5 ÅK and MMS-5 ÅCs and/or at least one metal oxide selected from the group of metal oxides consisting of Groups IIB, IIIA, IIIB, IVA and IVB metals.

It is provided herein a catalyst comprising at least one Mesoporous Linde Type A (MLTA) zeolite, alone or in combination with at least one ion exchanged Modified Molecular Sieve (MMS) selected from the group consisting of MMS-3 ÅK, MMS-3 ÅCs, MMS-4 ÅK, MMS-4 ÅCs, MMS-5 ÅK and MMS-5 ÅCs; and/or at least one metal oxide selected from the group consisting of groups IIB, IIIA, IIIB, IVA and IVB metals.

In an embodiment, the at least one metal oxide is selected from the group of consisting of Al, Ga, Hf, La, Si, Ti, Zn and Zr metal.

In another embodiment, the catalyst has a composition $u(Al_2O_3) \cdot v(TiO_2) \cdot w(ZnO) \cdot x(MMS) \cdot y(MLTA)$, wherein $0 \leq u \leq 3$ (wt); $0 \leq v \leq 3$ (wt); $0 \leq w \leq 3$ (wt); and $x+y \geq 0$.

In a further embodiment, wherein the catalyst has a composition $1(Al_2O_3) \cdot 1(TiO_2) \cdot 1(ZnO) \cdot 12.5(MMS) \cdot 4.2(MLTA)$.

In an additional embodiment, the catalyst has a composition $1(Al_2O_3) \cdot 1(TiO_2) \cdot 1(ZnO) \cdot 2.3(MMS) \cdot 8.3(MLTA)$.

In a further embodiment, the catalyst comprises MLTA.

In another embodiment, the catalyst has an average pore diameter between about 10 Å and about 500 Å.

In a further embodiment, the catalyst has a surface area between about 1 $m^2/g$ and about 100 $m^2/g$.

In another embodiment, the catalyst has a pore volume between about 0.01 $cm^3/g$ and 1 $cm^3/g$.

In an embodiment, the catalyst is in powdered, pelleted, an extruded form or coated on a metal or any suitable surface with or without an added binder.

In an alternated embodiment, the catalyst is calcined.

It is further provided the use of the catalyst encompassed herein in an esterification and/or transesterification reaction.

In an embodiment, it is further provided the use of the catalyst encompassed herein in the production of biodiesel.

It is also provided a method of performing an esterification and/or a transesterification of a starting material, comprising reacting the starting material with an alcohol in the presence of a catalyst, wherein the catalyst comprising at least one Mesoporous Linde Type A (MLTA) zeolite, alone or in combination with at least one ion exchanged Modified Molecular Sieve (MMS) selected from the group consisting of MMS-3 ÅK, MMS-3 ÅCs, MMS-4 ÅK, MMS-4 ÅCs, MMS-5 ÅK and MMS-5 ÅCs; and/or at least one metal oxide selected from the group consisting of groups IIB, IIIA, IIIB, IVA and IVB metals.

In an embodiment, the starting material comprises triglycerides, diglycerides, monoglycerides, fatty acids or a combination thereof.

In another embodiment, the starting material is a vegetable oil.

In another embodiment, the starting material is a used cooking oil.

In a further embodiment, the starting material is derived from animal fat.

In an embodiment, the starting material is tall oil.

In an additional embodiment, the starting material is a plant oil, animal fat, tall oil, or a combination thereof.

In an embodiment, the starting material is diluted with a solvent.

In a further embodiment, the starting material comprises a carboxylic acid, an ester or a combination thereof.

In another embodiment, the alcohol is an C1 to C10 aliphatic alcohol or a substituted aromatic group containing an alkyl alcohol.

In an embodiment, fatty acid esters are produced as a reaction product.

In an embodiment, carboxylic acid esters are produced as a reaction product.

In another embodiment, glycerol is produced as a reaction co-product.

In a further embodiment, the reaction is conducted at temperatures between about 160° C. and about 250° C.

In another embodiment, the reaction is conducted at pressures less than about 1000 psi.

In an embodiment, the reaction is conducted in a batch reactor.

In a further embodiment, the reaction is conducted continuously in a fixed bed reactor.

In a supplemental embodiment, the reaction is conducted with a ratio of alcohol to starting material equal to or greater than 0.5.

In an embodiment, the reaction is conducted at a ratio of volume of starting material per volume of catalyst per hour of between about 0.1 and about 2.

In another embodiment, the ester content after the esterification and/or transesterification is at least 90% for at least 60 days.

BRIEF DESCRIPTION OF THE DRAWINGS

Reference will now be made to the accompanying drawings.

FIG. 1 illustrates a continuous fixed bed process in accordance to an embodiment.

DESCRIPTION

The present disclosure relates to solid, heterogeneous catalyst compositions and use thereof in an esterification and/or transesterification reaction, that is in the production of alkyl esters from a starting material containing any one or more of the following: triglycerides, diglycerides, monoglycerides, free fatty acids, or a mixture thereof, and aromatic or aliphatic carboxylic acids.

Catalysts with large pore size can increase the accessibility of large molecules such as triglyceride to the catalyst active sites. The large pore size of mesoporous or macroporous catalysts allows a better diffusion of large substrate, enhances the efficiency of the catalyst which in turn reduces contact time and increases productivity. It is thus provided an improved catalyst comprising a MLTA zeolite and its use in producing carboxylic acid esters from various glycerides, high fatty acid containing glycerides and free fatty or carboxylic acids. The MLTA-containing catalysts as described herein are capable of esterification and transesterification reactions simultaneously under the same process conditions, requiring reduced contact time with increased space velocity.

The terms "oil", "feedstock", and "starting material" as used herein refer to a substance having any detectable triglycerides, diglycerides, monoglycerides and/or free fatty acid and/or carboxylic acid (whether aromatic or aliphatic) content, such as animal fats, vegetable oils, used cooking oils, and the likes. Examples of vegetable oils include, without limitation, canola oil, corn oil, soybean oil, palm oil, coconut oil, jatropha oil, camelina oil, cottonseed oil, flax seed oil, sunflower oil, tall oil and rapeseed oil. Examples of animal fats include, without limitation, beef tallow, pork lard, and the likes. Other further starting materials may also be suitable, such as glycerides present in or obtained from certain types of algae and the likes.

The term "heterogeneous" as used herein with respect to solid catalysts refers to any solid physical form of suitable catalyst, whether a catalyst is calcined or otherwise hardened, whether provided in powder, pellet, balled, or extruded form or anchored to a solid structure such as a molecular sieve of natural or synthetic solid-state composition. Such catalysts are generally not solubilized during the reaction and the majority of the catalyst is recoverable from the reaction products by simple filtration.

In an embodiment, a solid, heterogeneous catalyst for use in an esterification and/or transesterification reaction is provided. The catalyst comprises at least one MLTA zeolite and/or at least one ion exchanged type 3 Å, 4 Å, 5 Å zeolite (Modified Molecular Sieves, MMS), and/or at least one metal oxide. The catalyst according to the present disclosure may be used in the production of biodiesel that may be used as engine fuel.

In this embodiment, the MLTA zeolite has an average pore diameter between about 10 Å and about 500 Å. The MLTA may be synthesized by hydrothermal aging with tunable mesoporous structure using the amphiphilic organosilanes as a structure-directing agent, such as [3-(trimethoxysilyl)propyl]hexadecyldimethyl-ammonium chloride (TPHAC).

Alternatively, the structure-directing agent may be synthesized from a fatty acid ester, from a mixture of naturally occurring fatty acid esters obtained from natural triglycerides or from any other suitable agent or mixture in other embodiments.

The MMS may be obtained by exchanging one or more of the Na+ ions present in the microporous Type A Zeolites (Molecular Sieves or MS) with $K^+$ or $Cs^+$ ions. MS-3 Å have a general formula prior to ion exchange: $K_nNa_{(12-n)}[(AlO2)_{12}(SiO2)_{12}]\cdot xH_2O$; MS-3 Å after ion exchange with $K^+$ or $Cs^+$ results into MMS-3 ÅK with molecular formula: $K_nNa_{(12-n)}[(AlO_2)_{12}(SiO_2)_{12}]\cdot xH_2O$, and MMS-3 ÅCs with molecular formula: $Cs_mK_nNa_{(12-m-n)}[(AlO_2)_{12}(SiO_2)_{12}]\cdot xH_2O$, respectively. MS-4 Å have a general formula prior to ion exchange: $Na_{12}[(AlO_2)_{12}(SiO_2)_{12}]\cdot xH_2O$; MS-4 Å after ion exchange with $K^+$ or $Cs^+$ results into MMS-4 ÅK with molecular formula: $Cs_nNa_{(12-n)}[(AlO_2)_{12}(SiO_2)_{12}]\cdot xH_2O$, and MMS-4 ÅCs with molecular formula: $Cs_nNa_{(12-n)}[(AlO_2)_{12}(SiO_2)_{12}]\cdot xH_2O$, respectively. MS-5 Å have a general formula prior to ion exchange: $Ca_nNa_{(12-2n)}[(AlO_2)_{12}(SiO_2)_n]\cdot xH_2O$; MS-5 Å has naturally included $Ca^{++}$ ions. MS 5 Å after ion exchange with $K^+$ or $Cs^+$ results into MMS-5 ÅK with molecular formula: $K_mCa_nNa_{\{12-(m+2n)\}}[(AlO_2)_{12}(SiO_2)_{12}]\cdot xH_2O$ and MMS5 ÅCs with molecular formula: $Cs_mCa_nNa_{\{12-(m+2n)\}}[(AlO_2)_{12}(SiO_2)_{12}]\cdot xH_2O$, respectively.

In an embodiment, the MS and MLTA zeolite have $SiO_2/Al_2O_3$ ratios and pore diameters as shown in Table 1. The MS and MLTA zeolite may have any other suitable $SiO_2/Al_2O_3$ ratios and pore diameters as encompassed herein.

TABLE 1

MS and MLTA zeolite have $SiO_2/Al_2O_3$ ratios and pore diameters

| Molecular Sieves/Zeolite | $SiO_2/Al_2O_3$ Ratio | Pore Diameter |
| --- | --- | --- |
| MS-3 Å | 2:1 | 3 Å |
| MS-4 Å | 2:1 | 4 Å |
| MS-5 Å | 2:1 | 5 Å |
| MLTA | 2:1 | 10-500 Å |

In an embodiment, the metal oxide may be an oxide of Groups IIB, IIIA, IIIB, IVA, IVB metals in the periodic table, such as but not limited to oxides of aluminum, gallium, hafnium, lanthanum, silicon, titanium, zinc, or zirconium metals. Any other suitable metal oxide may be used as encompassed herein.

The metal oxide may be formed by calcination of a corresponding precursor salt such as chloride, nitrate, isopropoxide or hydroxide using known methods and protocols. These oxides may be calcined under vacuum, in the air or in the presence of a neutral gas (such as argon, nitrogen, helium and the likes) at temperatures between about 200° C. and about 1200° C., usually between about 400° C. and about 800° C.

In another embodiment, the catalyst has the following composition: $u(Al_2O_3)\cdot v(TiO_2)\cdot w(ZnO)\cdot x(MMS)\cdot y(MLTA)$, wherein $0\leq u\leq 3$ (wt); $0\leq v\leq 3$ (wt); $0\leq w\leq 3$ (wt); and $x+y\geq 0$, the coefficients u, v, w, x and y correspond to the weight (wt) ratios of the relevant components of the catalyst. For example, the catalyst may have a composition 1(Al$_2$O$_3$)·1(TiO$_2$)·1(ZnO)·12.5(MMS)·4.2(MLTA), 1(Al$_2$O$_3$)·1(TiO$_2$)·1(ZnO)·2.3(MMS)·8.3(MLTA), MLTA alone or any other suitable composition as encompassed herein.

The catalysts as encompassed herein may be provided in solid form, for example in powdered, pelleted, in extruded form or coated on a metal or any suitable surface, prepared with or without addition of a binder or an extruding aid. The catalysts may be calcined at a desired temperature before use.

The catalysts according to the present disclosure may notably be used in the production of biodiesel, as further discussed below. In accordance with one embodiment, there is provided a method for performing an esterification or a transesterification or simultaneous esterification and transesterification by mixing a starting material with an alcohol in one single step under the same process condition in presence of the solid, heterogeneous catalyst according to the present disclosure.

The starting material may accordingly be an oil, and/or may comprise triglycerides, diglycerides, monoglycerides, free fatty acids, or a mixture thereof and/or carboxylic acids; the starting material may further be diluted with an appropriate solvent. The method according to the present disclosure may be used to produce carboxylic acid ester and possibly glycerol as coproduct of transesterification when glycerides are used as starting material. Notably, as shown in the general catalyzed reactions represented below in Equations 6 through 8, soap is not produced as a byproduct of the reaction.

butane diol or a polyhydric alcohol such as glycerol, sorbitol, polyerythritol, polyethylene glycol, poly propylene glycol and the likes.

Further, ROH in equations 6 through 8 represents suitable alcohols, including without limitation: a C1 to C18 monohydric aliphatic alcohol such as methanol, ethanol, propanol, isopropanol, butyl alcohol, and stearyl alcohol; a monohydric aromatic alcohol such as benzyl alcohol or a substituted benzyl alcohol; a dihydric alcohol such as ethylene glycol, propylene glycol, and butanediol; or a polyhydric alcohol such as glycerol, sorbitol, polyerythritol, polyethylene glycol, and polypropylene glycol. Any other suitable alcohol may also be used in other embodiments.

In one embodiment, the esterification/transesterification/simultaneous esterification and transesterification reaction may be conducted at temperatures between about 160° C. and about 250° C., preferably between about 180° C. and about 225° C. Further, the reaction may be conducted at pressures of less than about 1000 psi, preferably between about 700 psi and about 900 psi. It is appreciated that such conditions may vary depending on the specific catalyst, starting material, and process mode chosen. The reaction with the catalyst according to the present disclosure may indeed be conducted in a batch, intermittent/semi continuous or continuous mode. In the continuous mode, the reactor may be a fixed bed reactor. The reaction may be conducted in one stage, in two successive stages or in any suitable number of successive stages. In a fixed bed reactor, the reaction may be conducted with a volume of oil (starting material) injected in the reactor per volume of catalyst per hour (VVH) of between about 0.1 h$^{-1}$ and about 1 h$^{-1}$ for the

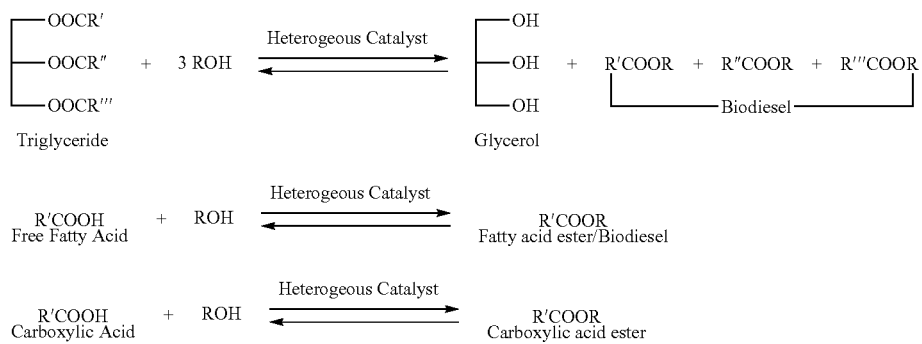

In the above equations, R', R" and R'" may be the same or different, and each may be a C1 to C22 linear or branched chain alkyl group, which may be further substituted with hydroxyl, alkoxy or halogens like chloro, bromo or fluoro or an aryl group that can be substituted with chloro, bromo, fluoro, nitro, lower alkoxy or lower alkyl such as methyl, ethyl, propyl, isopropyl or butyl which may be further substituted with halogens such as chloro, bromo, fluoro or a phenyl group that can be substituted with chloro, bromo, fluoro nitro, lower alkyl or alkoxy group. Further, each may represent an alkyl group of a monocarboxylic acid such as acetic, propionic, butyric, caproic, caprilic, capric, lauric, myristic, palmitic, oleic, stearic or a dicarboxylic acid such as adipic acid, which are in an ester form with a C1 to C18 monohydric aliphatic alcohol such as methyl, ethyl, propyl, isopropyl, butyl and stearyl alcohol, a monohydric aromatic alcohol such as benzyl or substituted benzyl alcohol or a dihydric alcohol such as ethylene glycol, propylene glycol, catalyst without MLTA and between about 0.1 h$^{-1}$ and about 2 h$^{-1}$ for the catalyst with MLTA. And the reaction is conducted with a ratio of alcohol to starting material equal to or greater than 0.5.

The catalysts according to the present disclosure provide an excellent yield, as further discussed below, and are insoluble in process medium, preventing elution and volume loss. The catalysts are also tolerant of free fatty acids and water generated during esterification process (free fatty acid and water do not affect the activity of the catalyst). Furthermore, the method according to the present disclosure does not require the use of a desiccant for continuous removal of the water generated during the esterification/transesterification/simultaneous esterification and transesterification of fatty acids.

Fatty acid esters and glycerol are produced as the reaction products when glycerides are used as feed oil.

EXAMPLES

All reagents and alcohols used in the following examples were of ACS grade. The triglyceride source/starting material was food grade canola oil with approximately 1% free fatty acids. All metal oxides, molecular sieves, carboxylic acids and other chemicals were purchased from Aldrich Chemical Co. Free Fatty acids used were prepared by hydrolyzing vegetable oils. Fatty acid methyl ester products were analyzed following ASTM D6584 protocols on Agilent Gas Chromatography Instrument.

Preparation of MMS-4 ÅK

Potassium exchanged molecular sieves were prepared by partial ion exchanging molecular sieves of molecular formula, $Na_{12}[(AlO_2)_{12}(SiO_2)_{12}]\cdot xH_2O$ (MS-4 Å). 80 g of MS-4 Å were suspended in 500 ml, 0.5 Molar aqueous solution of potassium hydroxide and heated under reflux for 5 h and allowed to cool to room temp. The exchanged molecular sieves were washed with distilled water repeatedly to remove excess potassium hydroxide. Obtained solid was dried at 120° C. overnight.

Preparation of MMS-4 ÅCs

Cesium exchanged molecular sieves were prepared by partial ion exchanging molecular sieves of molecular formula, $Na_{12}[(AlO_2)_{12}(SiO_2)_{12}]\cdot xH_2O$ (MS-4 Å). MS-4 Å (100 g) was suspended in 700 ml, 0.5 Molar aqueous solution of cesium chloride and heated under reflux for 5 h and allowed to cool to room temp. The exchanged molecular sieves were washed with distilled water repeatedly to remove excess cesium chloride. Obtained solid was dried at 120° C. overnight Preparation of MMS-5 ÅK Potassium exchanged molecular sieves were prepared by partial ion exchanging molecular sieves molecular formula, $Ca_nNa_{(12-n)}[(AlO_2)_{12}(SiO_2)_{12}]\cdot xH_2O\cdot MS-5$ Å (100 g) was suspended in 700 ml, 0.5 Molar aqueous solution of potassium hydroxide and heated under reflux for 5 h and allowed to cool to room temp. The exchanged molecular sieves were washed with distilled water repeatedly to remove excess cesium chlorides. Obtained solid was dried at 120° C. overnight Preparation of MMS-5 ÅCs Cesium exchanged molecular sieves were prepared by partial ion exchanging molecular sieves of molecular formula, $Ca_nNa_{(12-n)}[(AlO_2)_{12}(SiO_2)_{12}]\cdot xH_2O$. MS-5 Å (100 g) was suspended in 700 ml, 0.5 Molar aqueous solution of cesium chloride and heated under reflux for 5 h and allowed to cool to room temp. The exchanged molecular sieves were washed with distilled water repeatedly to remove excess cesium chloride. Obtained solid was dried at 120° C. overnight Preparation of MLTA Zeolite A mesopore-directing agent [3-(trimethoxysilyl) propyl] hexadecyldimethyl-ammonium chloride (TPHAC) (75 g) was added to a mixture of sodium metasilicate (185.2 g)), sodium hydroxide (159.1 g), sodium aluminate (89.4 g) and distilled water (1.4 L). The molar composition of the mixture was $1Al_2O_3/3.3\ Na_2O/2SiO_2/128H_2O/0.08TPHAC$. After this mixture was heated with stirring in 2 L flask for 4 h at 95° C., the crystallized zeolite product was filtered, washed with distilled water, dried at 110° C. and calcined at 550° C. in static air. The synthesized MLTA BET surface area is 14.52 m²/g, with an average pore diameter of 25.4 nm and an average pore volume 0.092 cm³/g when calculated according to the Barret-Joyner-Halenda (BJH) calculation scheme (BJH average pore diameter and BJH average pore volume).

Catalyst Preparation—General Method

Preparation of Catalysts C-I to C-IV

Catalysts C-I to C-IV (Table 2) were prepared by mixing various components in quantity presented in Table 2 and extruded, dried at 100° C. for 24 h and calcined at 550° C. for 3 hours. The calcined extrudate was washed with distilled water to remove excess KOH and recalcined at 550° C. for 3 hours.

TABLE 2

Catalysts C-I to C-IV

| Catalyst Preparation | Al₂O₃ g | ZnO g | TiO₂ g | H₂O ml | MMS-4 ÅK g | MLTA g | KOH g | Catalyst Composition |
|---|---|---|---|---|---|---|---|---|
| C-I | 30 | 30 | 30 | 200 | 250 | 0 | 0 | 1(Al₂O₃)•1(TiO₂)•1(ZnO)•8.3(MMS)•0(MLTA) |
| C-II | 2.4 | 2.4 | 2.4 | 35 | 30 | 10 | 3.43 | 1(Al₂O₃)•1(TiO₂)•1(ZnO)•12.5(MMS)•4.2(MLTA) |
| C-III | 12 | 12 | 12 | 260 | 27 | 100 | 8.8 | 1(Al₂O₃)•1(TiO₂)•1(ZnO)•2.3(MMS)•8.3(MLTA) |
| C-IV | 0 | 0 | 0 | 0 | 0 | 23.4 | 0 | MLTA |

The energy-dispersive X-ray spectroscopy (EDX) elemental analysis and pore textural properties of catalysts C-I, C-II, C-III and C-IV are listed in Table 3 below. BET surface area is in the range of 1 to 100 m²/g, BJH average pore diameter is in the range of 1 to 50 nm and BJH pore volume is in the range of 0.01 to 1 cm³/g.

TABLE 3

Catalysts C-I to C-IV properties

| Catalyst | O | Na | Al | Si | K | Ti | Zn | Surface area (m²/g) | Average diameter (nm) | Pore volume (cm³/g) |
|---|---|---|---|---|---|---|---|---|---|---|
| | | | | w/w % | | | | | | |
| C-I | 43 | 6.8 | 14.48 | 13.6 | 7.24 | 6.96 | 7.93 | 14.95 | 2.78 | 0.005 |
| C-II | 44.99 | 7.25 | 14.98 | 15.36 | 7.44 | 4.85 | 5.13 | 10.48 | 13.57 | 0.036 |
| C-III | 47.03 | 9.50 | 17.37 | 15.28 | 2.68 | 3.87 | 4.26 | 20.90 | 11.93 | 0.062 |
| C-IV | 51.83 | 13.91 | 15.45 | 18.81 | | | | 10.19 | 14.91 | 0.038 |

Continuous Fixed Bed Process

With reference to FIG. 1, a tubular stainless-steel reactor 10, equipped with pressure regulator 12, back pressure control valve 14 and temperature measurement device 16, was filled with the indicated catalyst 18. Reactants 20 and methanol 22 were introduced independently at the indicated ratios and flow rates from the top end of the reactor using metering pumps 24. The reactor tube 10 is heated by external heater 26. Pressure inside the reactor tube is maintained using a back-pressure valve 14. Hot effluents exiting the reactor are flashed into an expansion chamber 28 where methanol vapors are separated, condensed and recovered. Residue liquid is drained into a settling chamber 30, where the lower layer (containing glycerol 32) was separated from the upper layer containing methyl ester product 34. The process conditions and results of the experiments using different catalysts are reported in Table 4 below.

TABLE 4

Conditions and results with different catalysts

| Example | Catalyst | Temp. °C. | Pressure psi | VVH of Reactants $h^{-1}$ | Canola/FFA/MeOH vol/vol/vol | MG | DG w/w % | TG | E |
|---|---|---|---|---|---|---|---|---|---|
| | Prior art catalyst-I | 240 | 725 | 0.5 | $2^a$/0/1 | 4.35 | 1.3 | 0.02 | 94.1 |
| | Prior art catalyst-II | 200 | 725 | 0.5 | $1^a$/0/1 | 3.3 | 2.1 | 0.9 | 93.7 |
| 1 | C-I | 200 | 800 | 0.33 | 2/0/1 | 2.98 | 0.14 | 0.00 | 96.88 |
| 2 | C-II | 200 | 800 | 0.90 | 2/0/1 | 2.60 | 0.12 | 0.00 | 97.28 |
| 3 | C-III | 200 | 800 | 0.93 | 2/0/1 | 2.37 | 0.08 | 0.02 | 97.53 |
| 4 | C-IV | 195 | 800 | 1.60 | 2/0/1 | 2.92 | 0.17 | 0.00 | 96.91 |
| 5 | C-II | 200 | 800 | 0.17 | 0/1/1 | 0.00 | 0.00 | 0.00 | 100 |
| 6 | C-II | 200 | 800 | 0.18 | 1/0.18/1 | 3.09 | 0.74 | 0.55 | 95.62 |

$^a$Colza oil is used instead of Canola oil.

Reactants refers to the feed excluding methanol. MG, DG and TG refer to monoglycerides, diglycerides and triglycerides, respectively, present in product solution (in weight %, the product solution referring to the upper layer containing the methyl ester product and not including the lower layer containing glycerol) at the end of the catalytic reaction, while E refers to methyl esters content present in the solution (in weight %) at the end of the catalytic reaction. Catalysts C-I to C-IV all exhibit yields above 96% with a reaction temperature of 200° C., a ratio of methanol to canola (feed oil) of 1:2 (in volume) and a VVH of up to 1.60 $h^{-1}$. It is also appreciated that the catalysts according to the present disclosure allow simultaneous esterification and transesterification reactions under the same process conditions.

Process Conditions

With reference to FIG. 1, the process conditions including pressure, temperature and flow rate (VVH) were evaluated by using C-II from Table 2 as catalyst and canola oil as the feedstock.

The pressure variation effect was assessed by keeping the VVH constant at about 0.8 $h^{-1}$, temperature constant at about 210° C. and methanol/oil ratio at 0.6 while changing the process pressure. The results are shown in table 5.

TABLE 5

Pressure variation effect results

| Pressure psi | Temp. °C. | VVH $h^{-1}$ | MG | DG w/w % | TG | E |
|---|---|---|---|---|---|---|
| 860 | 210 | 0.80 | 2.84 | 0.10 | 0.00 | 97.06 |
| 760 | 210 | 0.80 | 2.90 | 0.16 | 0.02 | 96.92 |
| 700 | 210 | 0.80 | 2.39 | 0.15 | 0.03 | 97.43 |
| 640 | 210 | 0.80 | 3.08 | 0.15 | 0.02 | 96.75 |
| 610 | 210 | 0.80 | 2.34 | 0.12 | 0.01 | 97.53 |

The impact of the process temperature was further evaluated by keeping VVH constant at about 0.51 $h^{-1}$, the pressure constant at about 800 psi and methanol/oil ratio at 0.6 while changing the process temperature. The results are presented in Table 6.

TABLE 6

Impact of process temperature

| Temp. °C. | Pressure psi | VVH $h^{-1}$ | MG | DG w/w % | TG | E |
|---|---|---|---|---|---|---|
| 220 | 800 | 0.51 | 1.86 | 0.47 | 0.00 | 97.67 |
| 210 | 800 | 0.51 | 2.48 | 0.39 | 0.00 | 97.14 |
| 200 | 800 | 0.51 | 3.43 | 0.63 | 0.00 | 95.77 |
| 190 | 800 | 0.51 | 3.34 | 0.99 | 0.79 | 94.89 |

The impact of the VVH was further evaluated by keeping the pressure at about 800 psi, the process temperature at about 210° C. and methanol/oil ratio at 0.6 while changing the VVH. The results are shown in Table 7.

TABLE 7

Impact of VVH

| VVH $h^{-1}$ | Temp. °C. | Pressure psi | MG | DG w/w % | TG | E |
|---|---|---|---|---|---|---|
| 0.51 | 210 | 800 | 4.21 | 0.17 | 0.00 | 95.62 |
| 0.61 | 210 | 800 | 3.47 | 0.21 | 0.00 | 96.32 |
| 0.91 | 210 | 800 | 2.54 | 0.16 | 0.00 | 97.30 |
| 1.11 | 210 | 800 | 2.08 | 0.22 | 0.04 | 97.66 |

The impact of methanol/oil ratio was also investigated by keeping the pressure at about 800 psi, the process temperature at about 210° C. and VVH at 0.51 while changing alcohol/starting material ratio. The results are presented in Table 8.

TABLE 8

Impact of methanol/oil ratio

| MeOH/Oil ratio | Temp. °C. | Pressure psi | VVH h$^{-1}$ | MG | DG | TG | E |
|---|---|---|---|---|---|---|---|
| | | | | w/w % | | | |
| 0.5 | 210 | 800 | 0.51 | 2.48 | 0.39 | 0.00 | 97.14 |
| 0.6 | 210 | 800 | 0.51 | 1.96 | 0.59 | 0.00 | 97.45 |
| 0.8 | 210 | 800 | 0.51 | 1.21 | 0.30 | 0.00 | 98.49 |
| 1 | 210 | 800 | 0.51 | 0.98 | 0.00 | 0.00 | 99.02 |

The Scope of the Feeds

A variety of feedstocks including Canola oil, Olive oil, Safflower oil, Carinata oil, Camelina oil, Hemp seed oil and used cooking oil were subjected to the process in presence of the catalyst C-II with methanol/oil ratio at 0.6. The results are shown in Table 9.

TABLE 9

Variety of feedstocks processing with C-II

| Feed | Temp. °C. | Pressure psi | VVH h$^{-1}$ | MG | DG | TG | E |
|---|---|---|---|---|---|---|---|
| | | | | w/w % | | | |
| Canola oil | 210 | 800 | 0.51 | 2.48 | 0.39 | 0.00 | 97.14 |
| Olive oil | 210 | 800 | 0.51 | 2.00 | 0.26 | 0.00 | 97.74 |
| Safflower oil | 210 | 800 | 0.51 | 2.34 | 0.27 | 0.00 | 97.40 |
| Carinata oil | 210 | 800 | 0.51 | 2.09 | 0.24 | 0.00 | 97.67 |
| Camelina | 210 | 800 | 0.51 | 1.83 | 0.25 | 0.00 | 97.91 |
| Hemp seed oil | 210 | 800 | 0.51 | 1.80 | 0.24 | 0.00 | 97.96 |
| Used Cooking oil | 210 | 800 | 0.51 | 2.88 | 0.26 | 0.00 | 96.86 |

Catalyst Stability

The stability of catalyst C-II was investigated in the continuous fixed bed reactor. The transesterification of Canola oil over the catalyst C-II was performed under the fixed reaction condition at a temperature of 200° C., a pressure between 600 and 1000 psi, a VVH of 0.9 h$^{-1}$ and methanol/oil ratio at 0.6. The results in Table 10 show that the catalyst C-II exhibited the same performance over a 60-days period without any loss of catalytic activity.

TABLE 10

Long Term Run of Fixed Bed Transesterification of Canola Oil

| Duration (day) | MG | DG | TG | E |
|---|---|---|---|---|
| | w/w % | | | |
| 1 | 2.60 | 0.12 | 0.00 | 97.28 |
| 30 | 3.32 | 0.04 | 0.00 | 96.64 |
| 60 | 1.51 | 0.08 | 0.00 | 98.41 |

The above-described embodiments of the present disclosure are intended to be examples only. Alterations, modifications and variations may be affected to the particular embodiments by those skilled in the art without departing from the scope of the invention, which is defined solely by the claims appended hereto.

What is claimed is:

1. A catalyst comprising:
   at least one Mesoporous Linde Type A (MLTA) zeolite, alone or in combination with:
   at least one ion exchanged Modified Molecular Sieve (MMS) selected from the group consisting of MMS-3 ÅK, MMS-3 ÅCs, MMS-4 ÅK, MMS-4 ÅCs, MMS-5 ÅK and MMS-5 ÅCs; and/or
   at least one metal oxide selected from the group consisting of groups IIB, IIIA, IBB, IVA and IVB metals, wherein the catalyst has an average pore diameter between about 10 Å and about 500 Å, a surface area between about 1 m$^2$/g and about 100 m$^2$/g, and/or a pore volume between about 0.01 cm$^3$/g and 1 cm$^3$/g.

2. The catalyst of claim 1, wherein the at least one metal oxide is selected from the group of consisting of Al, Ga, Hf, La, Si, Ti, Zn and Zr metal.

3. The catalyst of claim 1, wherein the catalyst has a composition u(Al$_2$O$_3$)·v(TiO$_2$)·w(ZnO)·x(MMS)·y(MLTA), wherein 0≤u≤3 (wt); 0≤v≤3 (wt); 0≤w≤3 (wt); and x+y≥0.

4. The catalyst of claim 3, wherein the catalyst has a composition 1(Al$_2$O$_3$)·1(TiO$_2$)·1(ZnO)·12.5(MMS)·4.2 (MLTA) or 1(Al$_2$O$_3$)·1(TiO$_2$)·1(ZnO)·2.3(MMS)·8.3 (MLTA).

5. A method of performing an esterification and/or a transesterification of a starting material, comprising reacting the starting material with an alcohol in the presence of a catalyst as defined in claim 1.

6. The method of claim 5, wherein the starting material comprises triglycerides, diglycerides, monoglycerides, fatty acids or a combination thereof.

7. The method of claim 6, wherein the starting material is a vegetable oil.

8. The method of claim 6, wherein the starting material is a used cooking oil.

9. The method of claim 6, wherein the starting material is derived from animal fat.

10. The method of claim 6, wherein the starting material is tall oil.

11. The method of claim 6, wherein the starting material is a plant oil, animal fat, tall oil, or a combination thereof.

12. The method of claim 5, wherein the starting material comprises a carboxylic acid, an ester or a combination thereof.

13. The method of claim 5, wherein the alcohol is an C1 to C10 aliphatic alcohol or a substituted aromatic group containing an alkyl alcohol.

14. The method of claim 5, wherein fatty acid esters, glycerol and/or carboxylic acid esters are produced as a reaction product.

15. The method of claim 5, wherein the reaction is conducted at temperatures between about 160° C. and about 250° C. and/or at pressures less than about 1000 psi.

16. The method of claim 5, wherein the reaction is conducted in a batch reactor or continuously in a fixed bed reactor.

17. The method of claim 16, wherein the reaction is conducted with a ratio of alcohol to starting material equal to or greater than 0.5.

18. The method of claim 16, wherein the reaction is conducted at a ratio of volume of starting material per volume of catalyst per hour of between about 0.1 and about 2.

19. The method of claim 16, wherein the ester content after the esterification and/or transesterification is at least 90% for at least 60 days.

* * * * *